United States Patent
Trotz et al.

(10) Patent No.: US 7,230,244 B2
(45) Date of Patent: Jun. 12, 2007

(54) METHOD AND APPARATUS FOR THE DETECTION OF TERAHERTZ RADIATION ABSORPTION

(75) Inventors: Seth Trotz, Littleton, MA (US); Peter James Coyle, Newtown, PA (US)

(73) Assignee: Sarnoff Corporation, Princeton, NJ (US)

( * ) Notice: Subject to any disclaimer, the term of this patent is extended or adjusted under 35 U.S.C. 154(b) by 249 days.

(21) Appl. No.: 10/845,820

(22) Filed: May 14, 2004

(65) Prior Publication Data

US 2004/0227088 A1 Nov. 18, 2004

Related U.S. Application Data

(60) Provisional application No. 60/471,381, filed on May 16, 2003, provisional application No. 60/530,508, filed on Dec. 18, 2003.

(51) Int. Cl.
*G01J 5/02* (2006.01)
*G01N 21/17* (2006.01)
(52) U.S. Cl. ................................. 250/339.12
(58) Field of Classification Search ............ 250/339.12
See application file for complete search history.

(56) References Cited

U.S. PATENT DOCUMENTS

| | | | |
|---|---|---|---|
| 5,789,750 A | 8/1998 | Nuss | 250/338.1 |
| 6,335,625 B1 * | 1/2002 | Bryant et al. | 324/637 |
| 6,345,545 B1 * | 2/2002 | Linker et al. | 73/863.23 |
| 2001/0049926 A1 | 12/2001 | Davis | 55/385.2 |
| 2003/0085348 A1 * | 5/2003 | Megerle | 250/287 |
| 2004/0053421 A1 | 3/2004 | Nguyen et al. | 436/172 |
| 2004/0056016 A1 * | 3/2004 | Tian et al. | 219/408 |

OTHER PUBLICATIONS

Chen, et al., "THz spectroscopic investigation of 2,4-dinitrotoluene," Chemical Physics Letters 400 (2004) 357-361.

* cited by examiner

*Primary Examiner*—David Porta
*Assistant Examiner*—Christopher Webb
(74) *Attorney, Agent, or Firm*—Lowenstein Sandler PC (57) ABSTRACT

The invention is a method and apparatus for the detection of terahertz radiation. In one embodiment, frequency modulated spectroscopy is performed on a swept source of coherent far infrared electromagnetic radiation that is focused on a target. A beam of radiation passes through a cell in which the target is housed, losing energy as certain frequencies are absorbed by contaminants in the target. A detector is positioned to determine how much energy is lost by the radiation (e.g., which frequencies fail to transmit through the cell), thereby indicating the presence of contaminants in the target.

34 Claims, 6 Drawing Sheets

METHOD AND APPARATUS FOR THE DETECTION OF TERAHERTZ RADIATION ABSORPTION

CROSS REFERENCE TO RELATED APPLICATIONS

This application claims the benefit of U.S. Provisional Patent Application Ser. No. 60/471,381, filed May 16, 2003 (titled "Terahertz Source and Applications"), and of U.S. Provisional Patent Application No. 60/530,508, filed Dec. 18, 2003 (titled "An Autonomous Rapid Facility Chemical Agent Monitor Via Smith-Purcell Terahertz Spectrometry"), both of which are herein incorporated by reference in their entireties.

FIELD OF THE INVENTION

The present invention generally relates to the detection of chemical and biological contaminants, and more particularly relates to the detection of terahertz radiation absorption.

BACKGROUND OF THE INVENTION

There is an increasing demand for systems for military, private or individual use that are capable of detecting and analyzing chemical and biological contaminants, such as explosives (e.g., TNT or DNT). One method of detecting such contaminants uses rotational microwave spectroscopy. The rotational and vibrational modes of molecules (e.g., contaminant molecules) have energies that naturally correspond to energies of photons in a spectrum of radiation. A source generates radiation that interacts with contaminant molecules present in a "target" to be analyzed, so that specific frequencies of emitted radiation are absorbed by the molecules. A detector is positioned to identify the frequencies that fail to transmit through the target, and the failure of a particular frequency to transmit can indicate the presence of a specific absorbing contaminant.

The far infrared (or terahertz) spectrum of radiation is particularly well-suited for use in systems such as that described above, because the spectrum corresponds to the vibrational and rotational modes of many chemicals, including explosives, and contains a great deal of signature information. Unfortunately, work in the terahertz spectrum is made extremely difficult and inconvenient by a lack of coherent sources of radiation that can operate continuously and tune over a wide range of the terahertz wavelength spectrum.

Therefore, there is a need in the art for a terahertz system that can be used to detect the presence of chemical and biological contaminants.

SUMMARY OF THE INVENTION

In one embodiment, the invention is a method and apparatus for the detection of terahertz radiation. In one embodiment, frequency modulated spectroscopy is performed on a swept source of coherent terahertz radiation that is focused on a target. A beam of radiation passes through a cell in which the target is housed, losing energy as certain frequencies are absorbed by contaminants (e.g., target molecules or compounds of interest) in the target. A detector is positioned to determine how much energy is lost by the radiation (e.g., which frequencies fail to transmit through the cell), thereby indicating the presence of contaminants in the target.

In another embodiment, radiation is funneled into a microwave cavity. Certain wavelengths of radiation cause electrons in the microwave cavity to gain energy, and the increase in energy is observed by a measurement device such as an ammeter.

BRIEF DESCRIPTION OF THE DRAWINGS

So that the manner in which the above recited embodiments of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures.

DETAILED DESCRIPTION

A method and apparatus are provided for the detection of terahertz radiation absorption by a target to indicate the presence of contaminants. A source of coherent far infrared radiation is used in conjunction with a detection system to facilitate a convenient and effective method of performing frequency modulation spectroscopy in the far infrared spectrum.

Figure 1:
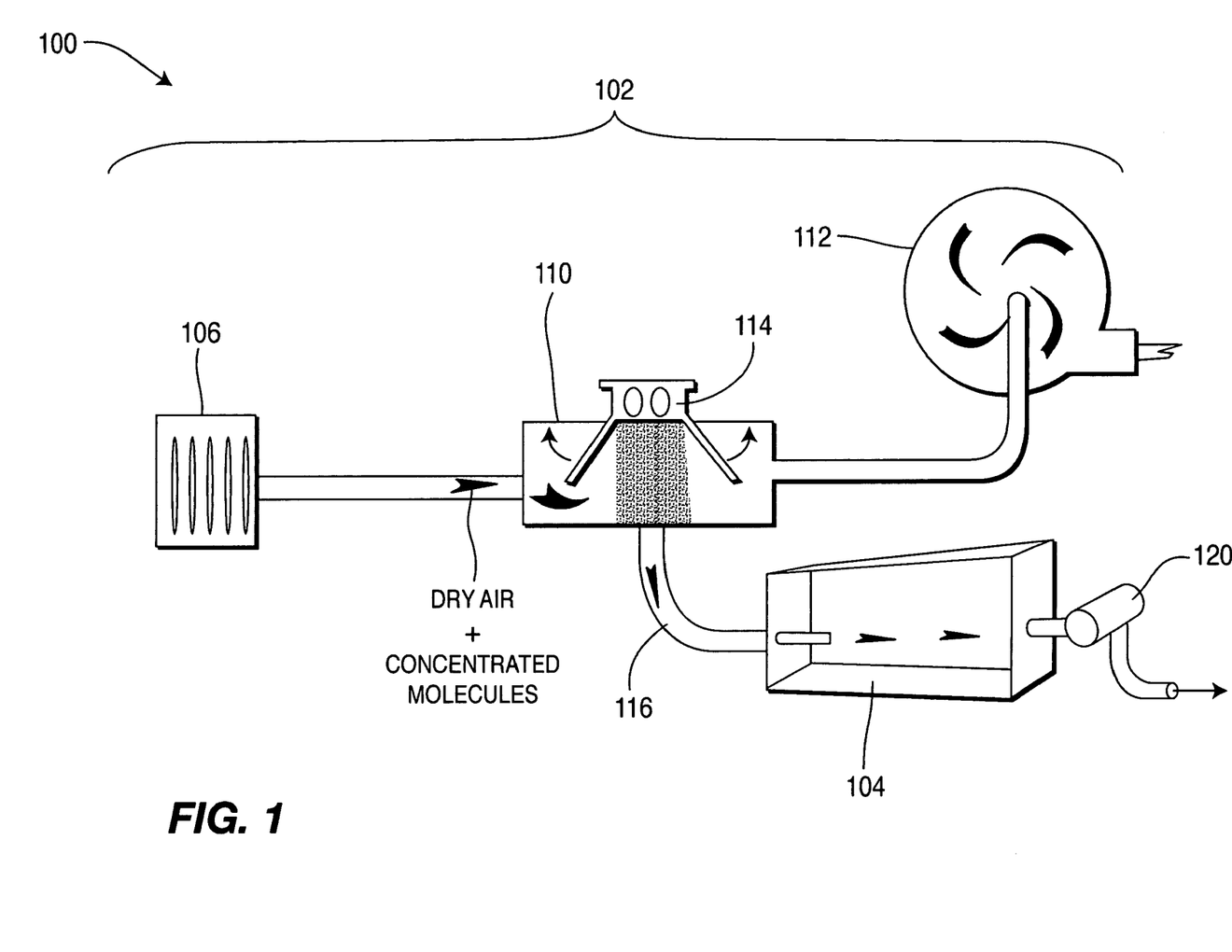
FIG. 1 illustrates a perspective view of one embodiment of a system for concentrating and analyzing a sample for the detection of contaminants.

FIG. 1 illustrates a perspective view of one embodiment of a system 100 for concentrating and analyzing a sample for the detection of contaminants such as explosives. The system 100 comprises a concentrator 102 and a terahertz detection system 104. The concentrator 102 is coupled to the detection system 104 to provide a concentrated sample to the detection system 104 for analysis. Concentrating the sample allows the detection system 104 to work more effectively because the vapor densities of most contaminants of interest (e.g., explosives or other chemicals) are on the order of parts per trillion and would therefore be otherwise difficult to detect in a diluted sample.

The concentrator 102 comprises a pre-concentrator 106, a heat exchanger 110 and a second-stage sampling pump 112.

The pre-concentrator 106 includes a sampling fan (not shown) for drawing in a sample in gaseous or liquid form, and is adapted to heat the sample to boil off contaminant vapor molecules. In one embodiment, the sample is heated in a manner that evaporates substantially all extraneous liquid or gas in the sample, so that a resultant absorption signal is not obfuscated. In one embodiment, this is accomplished by a fractional distillation of the liquid, wherein the remaining particles are subsequently heated for spectroscopy.

The heat exchanger 110 is coupled to both the pre-concentrator 106 and the second-stage sampling pump 112. The second-stage sampling pump 112 is adapted to draw the sample from the pre-concentrator 106 to the heat exchanger 110. The second stage sampling pump 112 also draws a small amount of inert gas through heat exchanger 110 in order to aid in the concentration of the contaminant vapor molecules. The heat exchanger 110 is adapted to condense the contaminant vapor molecules, which are then drawn out of the heat exchanger 110 and through the detection system 104 for analysis.

The heat exchanger 110 is adapted to be cooled so that the contaminant vapor molecules received from the pre-concentrator 106 condense on an interior surface of the heat exchanger 110. In one embodiment, the heat exchanger 110 is adapted to be cooled for a pre-determined interval of time to allow a quantity of vapor molecules to condense. The heat exchanger 100 is further adapted to be sealed and heated to evaporate the vapor molecules that are absorbed onto the interior surface of the heat exchanger 110. The heat exchanger 110 is then evacuated by a pump 120 that is coupled to the detector system 104 to draw the contaminant vapor molecules through the detector system 104. In one embodiment, a sonic orifice 116 couples the heat exchanger 110 to the detection system 104 to control the pressure within the detection system 104. The heat exchanger 110 is designed to have minimal pressure drop in the ambient pressure vapor flow direction.

In one embodiment, the heat exchanger 110 is cooled by a thermal electric cooler 114 during the condensation phase. By reversing the thermal electric cooler 114, the heat exchanger 110 may be heated for the evaporation phase. In another embodiment, electrical resistance heaters are used in combination with the thermal electric cooler 114 to facilitate evaporation. In yet another embodiment, the heat exchanger 110 is cooled by impingement cooling.

Figure 2:
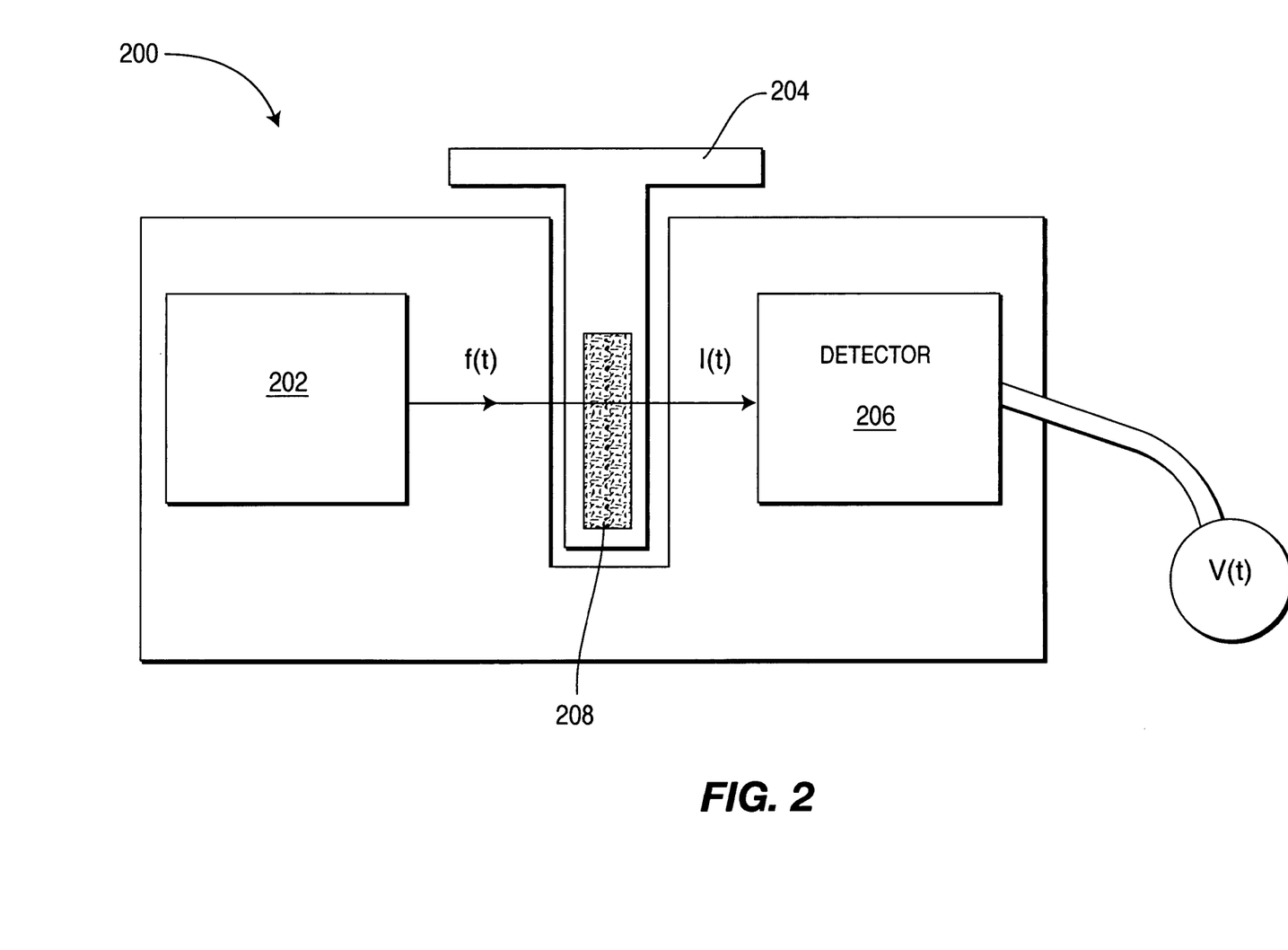
FIG. 2 illustrates a perspective view of one embodiment of a detection system for performing frequency modulated spectroscopy in the terahertz spectrum.

FIG. 2 illustrates a perspective view of one embodiment of a detection system 200 for detecting terahertz radiation absorption by a sample 208 (e.g., a low-pressure gas). The system 200 is a turn-key spectrometer maintained at a vacuum and comprises a radiation source 202, a cell 204, and a detector 206. The radiation source 202 provides frequency modulated output (i.e., terahertz radiation) f(t) to the cell 204. The output f(t) passes through the sample 208, which is contained within the cell 204, and molecules in the sample 208 may absorb some frequencies of radiation from the source output f(t), depending on the nature and quantity of chemical and/or biological agents present within the sample 208. Consequently, the intensity of the radiation that entered the cell 204 decreases and an intensity modulated beam of radiation I(t) exits the cell 204. The intensity modulated beam I(t) passes into the detector 206, which registers a voltage V(t) that may be used to calculate the intensity differential of the emitted radiation across the cell 204.

In one embodiment, the radiation source 202 is a far infrared swept source such as any of the sources disclosed in co-pending, commonly assigned U. S. patent application filed simultaneously herewith by Trotz et al. (titled "Method and Apparatus for Generating Terahertz Radiation"), having Ser. No. 10/845,821. The cell 204 has far infrared transmissive walls to allow the frequency modulated source output f(t) and the intensity modulated beam I(t) to pass therethrough. In one embodiment, the detector 206 is a broadband detector.

Figure 3:
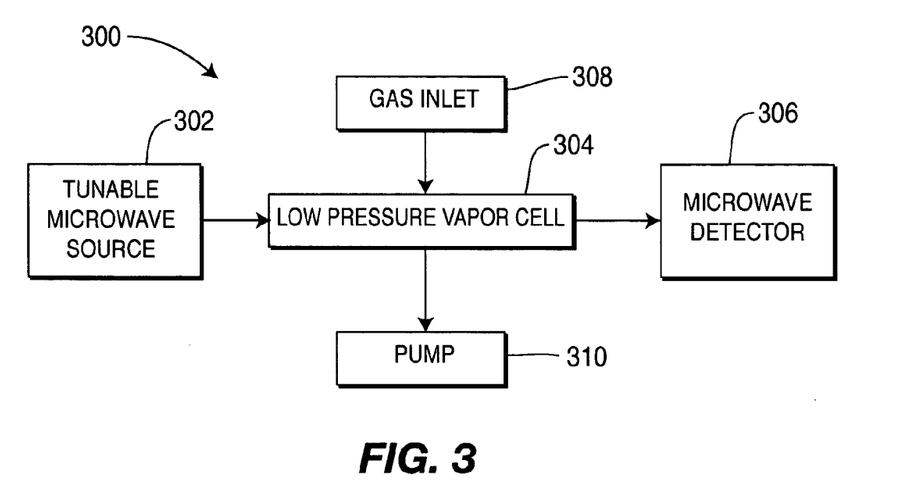
FIG. 3 illustrates a schematic diagram of one embodiment of a solid state detection system for detecting terahertz radiation absorption by a sample.

FIG. 3 illustrates a schematic diagram of one embodiment of a solid state detection system 300 for detecting terahertz radiation absorption by a sample (e.g., a low-pressure gas). The system 300 is contained within a vacuum and is similar to the spectrometer 200 illustrated in FIG. 2; however, the system 300 may be particularly advantageous in detecting the presence of explosives such as TNT or DNT, among others. The system 300 comprises a tunable microwave source 302, a low-pressure vapor cell 304 and a microwave detector 306. The microwave source 302 is coupled to the vapor cell 304 so as to pass radiation in the far infrared spectrum through the vapor cell 304. The vapor cell 304 is also coupled to the detector 306, which is positioned to detect the frequencies of radiation that exit the vapor cell 304 (i.e., the frequencies that are not absorbed by molecules in the sample). A gas inlet 308 is coupled to the vapor cell 304 to provide the sample to the system 300. In one embodiment, the gas inlet is similar to the sonic orifice 116 illustrated in FIG. 1. A pump 310 is also coupled to the vapor cell 304 to maintain a low pressure differential, and in one embodiment, the pump 310 is similar to the pump 120 illustrated in FIG. 1.

In one embodiment, the microwave source 302 is an Impact Avalanche Transit Time (IMPATT) multiplier whose input is low frequency microwaves produced by a solid state oscillator. The low range of frequencies at which the microwave source 302 operates makes it ideally suited for the detection of explosives such as TNT or DNT, which have peak rotational absorptions in the low terahertz range. In another embodiment, the microwave source 302 is a far infrared swept source such as any of the sources disclosed in co-pending, commonly assigned U.S. patent application filed simultaneously herewith by Trotz et al. (titled "Method and Apparatus for Generating Terahertz Radiation"), having Ser. No. 10/845,582. Furthermore, the production of a range of frequencies by the microwave source 302 allows the detector 306 to observe variations in the absorption of the sample with frequency, which enables more accurate identification of explosives. In one embodiment, the detector 306 is cryogenically cooled to detect the decrease in signal of the radiation that passes through the sample in the vapor cell 304.

Figure 4:
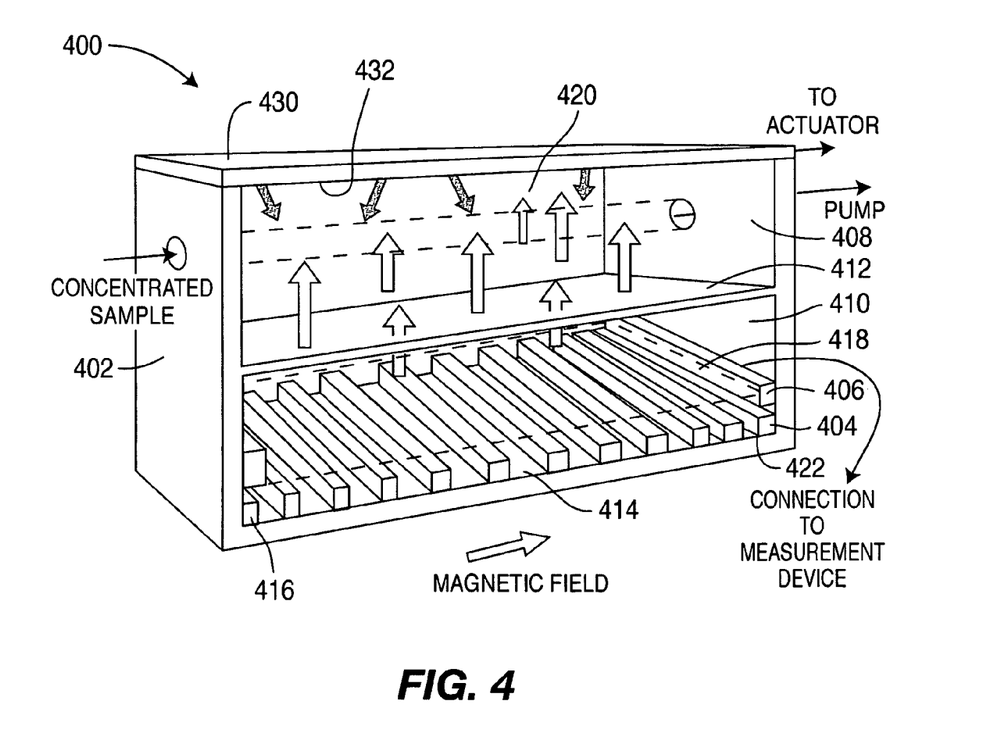
FIG. 4 illustrates a perspective view of an embodiment of a detection system for detecting terahertz radiation absorption by a gaseous sample using generated Smith-Purcell radiation.

FIG. 4 illustrates a perspective view of an embodiment of a detection system 400 for detecting terahertz radiation absorption by a sample. The system 400 comprises a microwave cavity 402, a grating 404 and a collector 406. The microwave cavity 402 further comprises a lid 430 and a terahertz transmissive window 412 that splits the microwave cavity 402 into two regions: a sample chamber 408 and a vacuum chamber 410. The lid 430 has a reflective surface 432 that is positioned to face the transmissive window 412. The grating 404 is positioned on a flat surface 414 of the vacuum chamber 410 that faces the window 412. The collector 406 is positioned at a second end 416 of the grating 404.

A concentrated sample gas is provided to the sample chamber 408, for example via sonic orifice 116 (FIG. 1), for analysis. Sample analysis is facilitated by exploiting a phenomenon known as Smith-Purcell radiation. When an electron beam 418 is passed close to the grating 404 from a first end 416 to a second end 422, the beam 418 is "bunched" by the grating 404, and radiation waves 420 are generated that propagate at an angle substantially normal to the electron beam 418. The radiation waves 420 pass through the window 412 and into the sample chamber 408, where the radiation waves encounter the reflective surface 432 of the lid 430. The reflective surface 432 discretizes the radiation waves into bands. A magnetic field having lines substantially parallel to the electron beam 418 acts on the beam 418 and bends the path of the beam 418 approximately when the beam 418 reaches the second end 422 of the grating 404.

As discussed above, some frequencies of the emitted radiation 420 may be absorbed by molecules in the sample gas contained in the sample chamber 408. Absorption of frequencies will cause the electron beam 418 to lose energy. The more energy that is lost by the electron beam 418, the more the beam 418 will bend. The collector 406 intercepts the electron beam, and a measurement device coupled to the collector 406 receives information from the collector to determine the amount of energy lost by the electron beam. Specifically, the information intercepted by the collector 406 demonstrates the degree to which the electron beam 418 bends (i.e., the locations at which the beam 418 hits the collector 406) and the energy of the beam 418 after it passes over the grating 404 (i.e., how much current hits the collector 406) for a particular emitted frequency. Thus, the absorption of the radiation 420 at a particular frequency can be indirectly measured by performing energy spectroscopy on the electron beam 418 (i.e., by determining the amount of energy lost by the beam 418). In one embodiment, the energy lost by the beam may be estimated by calculating the Lorentz force on the beam due to the magnetic field, wherein the velocity (which corresponds to the voltage) of the beam is known. The energy lost is due to the emission of photons corresponding to the wavelengths of radiation that are being absorbed. In another embodiment, electron beam energy may be measured by slowing the beam down electrostatically, e.g., using an electric field, to determine a voltage on the beam.

The system 400 is tunable by varying the voltage of the electron beam 418. That is, the frequency of the radiation waves 420 emitted by passing the electron beam 418 over the grating 404 is a function of the grating period (i.e., spacing of the grating 404) and the voltage of the electron beam 418. Thus, the system 400 is tunable over a spectrum of terahertz frequencies to facilitate accurate detection of contaminants in a sample. In another embodiment, the lid 430 may be coupled to an actuator to alter the position of the reflective surface 432, so that the bands of discretized radiation reflected by the reflective surface 432 can be controlled.

Figure 5:
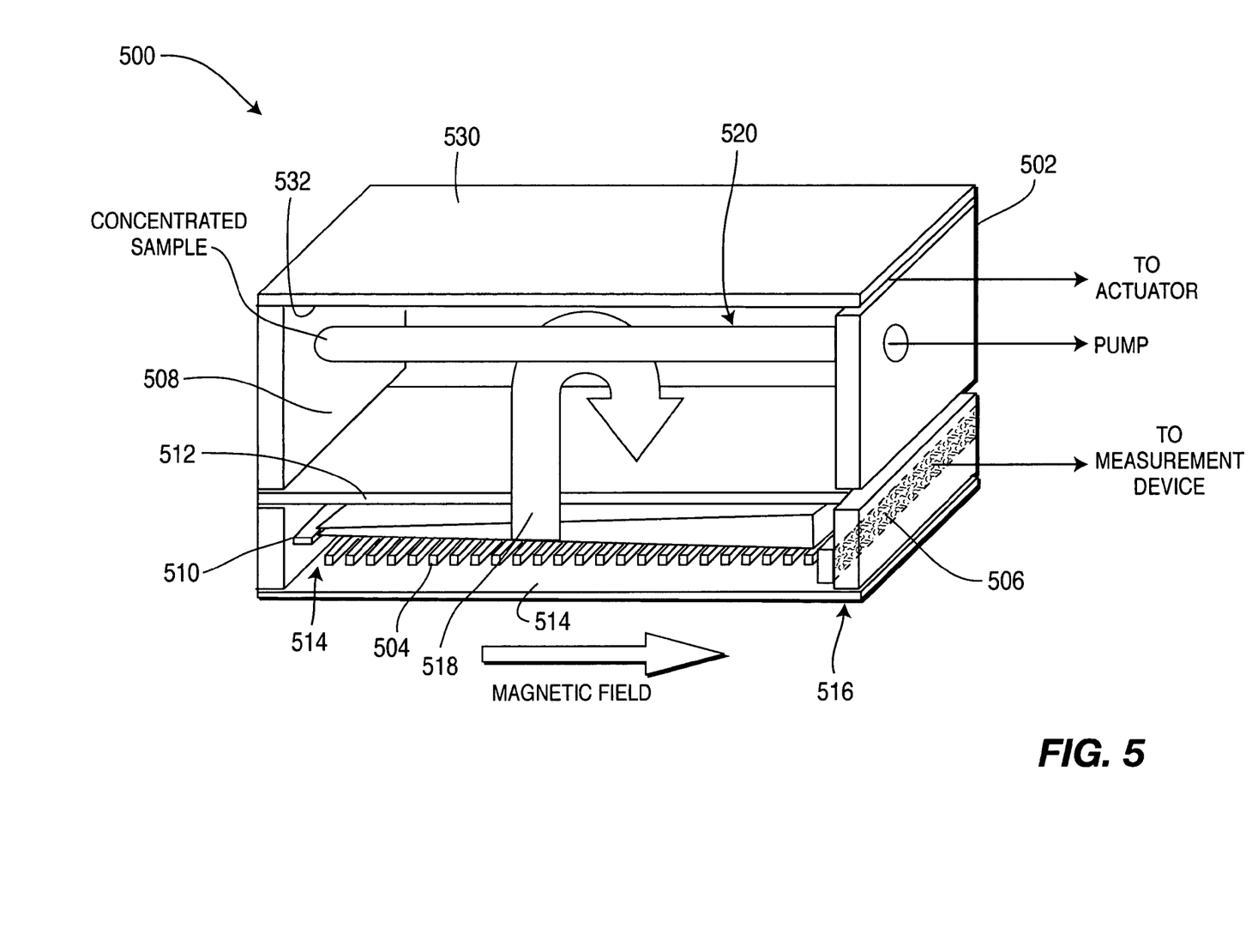
FIG. 5 is a perspective view of an embodiment of a detection system for detecting terahertz radiation absorption by a liquid sample.

FIG. 5 is a perspective view of an embodiment of a detection system 500 for detecting terahertz radiation absorption by a sample in which the sample is suspended in a liquid rather than a gas. The system 500 is substantially similar to the system 400 illustrated in FIG. 4 and comprises a microwave cavity 502, a grating 504 and a collector 506. The microwave cavity 502 further comprises a lid 530 and a terahertz transmissive window 512 that splits the microwave cavity 502 into two regions: a sample chamber 508 and a vacuum chamber 510. The grating 504 is positioned on a flat surface 514 of the vacuum chamber 510 that faces the window 512. The collector 506 is positioned at one end 516 of the grating 504, opposite the point of entry for an electron beam. The lid 530 has a reflective surface 532 positioned to face the transmissive window 512.

A sample tube 520 spans the sample chamber 508 and is positioned substantially parallel to the grating 504. A sample for analysis is concentrated within a liquid that is contained within the sample tube 520. When an electron beam is passed close to the grating 504 from a first end 514 to the second end 516, the beam is "bunched" by the grating 504, and radiation waves 518 are generated that propagate at an angle substantially normal to the electron beam. The radiation waves 518 pass through the window 512 and into the sample chamber 508, where the radiation is discretized into bands by the reflective surface 532 of the lid 530. A magnetic field having lines substantially parallel to the electron beam acts on the beam and bends the path of the beam approximately when the beam reaches the second end 516 of the grating 504.

As discussed above, some wavelengths of the emitted radiation may be absorbed by molecules in the sample contained within the sample tube 520. Absorption of wavelengths will cause the electron beam to lose energy, and the more energy that is lost by the electron beam, the more the beam will bend. The collector 506 intercepts the electron beam, and a measurement device coupled to the collector 506 receives information from the collector to determine the amount of energy lost by the electron beam. Specifically, the information intercepted by the collector 506 demonstrates the degree to which the electron beam bends (i.e., the locations at which the beam hits the collector 506) and the energy of the beam after it passes over the grating 504 (i.e., how much current hits the collector 506) for a particular emitted frequency. Thus, the absorption of the radiation at a particular frequency can be indirectly measured by performing energy spectroscopy on the electron beam (i.e., by determining the amount of energy lost by the beam.

The system 500 is tunable by several methods. For instance, the voltage of the electron beam may be varied. Alternatively, a dynamic (i.e., variable-period) grating 504 could be incorporated into the system. Finally, an actuator could be coupled to the lid 530 to vary the position of the reflective surface 532. Thus, the system 500 is tunable over a spectrum of terahertz frequencies to facilitate accurate detection of contaminants in a sample.

The system 500, in which a sample is introduced for analysis via a liquid rather than a gas, may be particularly well-suited for the detection of chemical agents and contaminants, such as pharmaceuticals or narcotics. This is because the molecules in such substances have a tendency to bind to each other, or to proteins or other surfaces. This tendency of the molecules to bind alters the rotational modes of the molecules and restricts the ranges of motion, which in turn modifies a rotational spectrum of the molecules.

Figure 6:
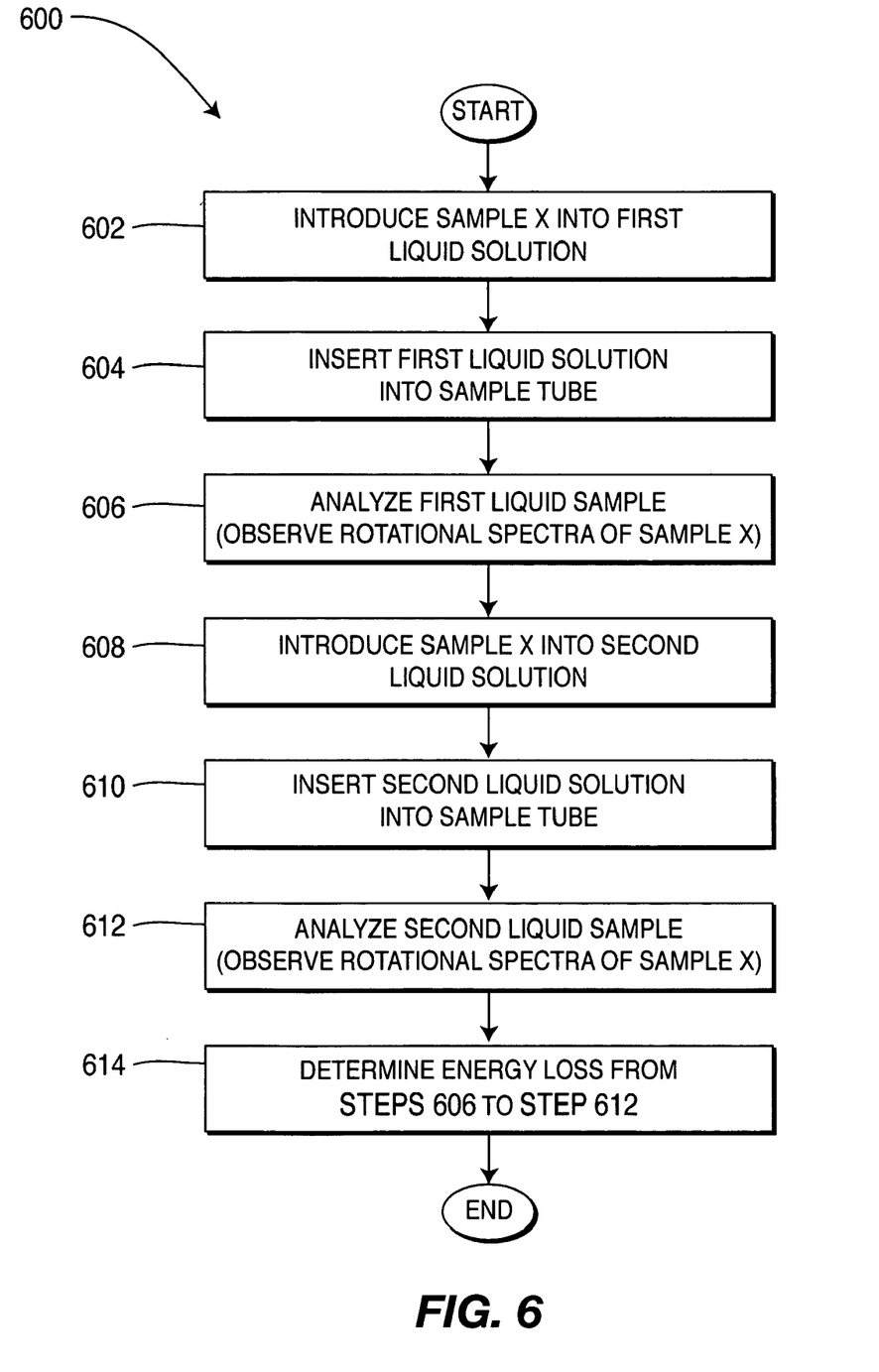
FIG. 6 is a flow diagram illustrating one embodiment of a method for detecting terahertz radiation by a liquid sample using the system illustrated in FIG. 5.

FIG. 6 illustrates a flow diagram of one embodiment of a method 600 for detecting terahertz radiation absorption by a liquid sample using the system 500 illustrated in FIG. 5, in which a sample potentially containing molecules of one or more contaminants is introduced into a first liquid solution at step 602, and this first liquid solution is inserted into the sample tube 520 for analysis at step 604. The rotational spectrum of the molecules in the solution is analyzed by the system 500 by the method described above with reference to FIG. 5, at step 606. Following analysis of the first liquid solution, a quantity of the same sample material is introduced into a second liquid solution containing at least one binding agent (e.g., a protein) that may bind to some of the molecules in the sample material, at step 608. In one embodiment, the binding agent binds to molecules of a contaminant present within the second liquid solution (e.g., introduced via the sample material). The second solution is inserted into the sample tube 520 at step 610 and is analyzed by the system 500 at step 612 to determine the altered rotational spectrum of the second liquid sample molecules. By comparing the rotational spectra with regard to the first and second liquid samples at step 614 (i.e., by determining the energy lost in the analyses of the first and second liquid samples), the geometry of the protein-molecule bond can be derived. Thus, the degree to which the rotational spectrum of the first and second liquid sample molecules is altered can be used indirectly to detect and identify molecules of a contaminant present within the sample material.

Figure 7:
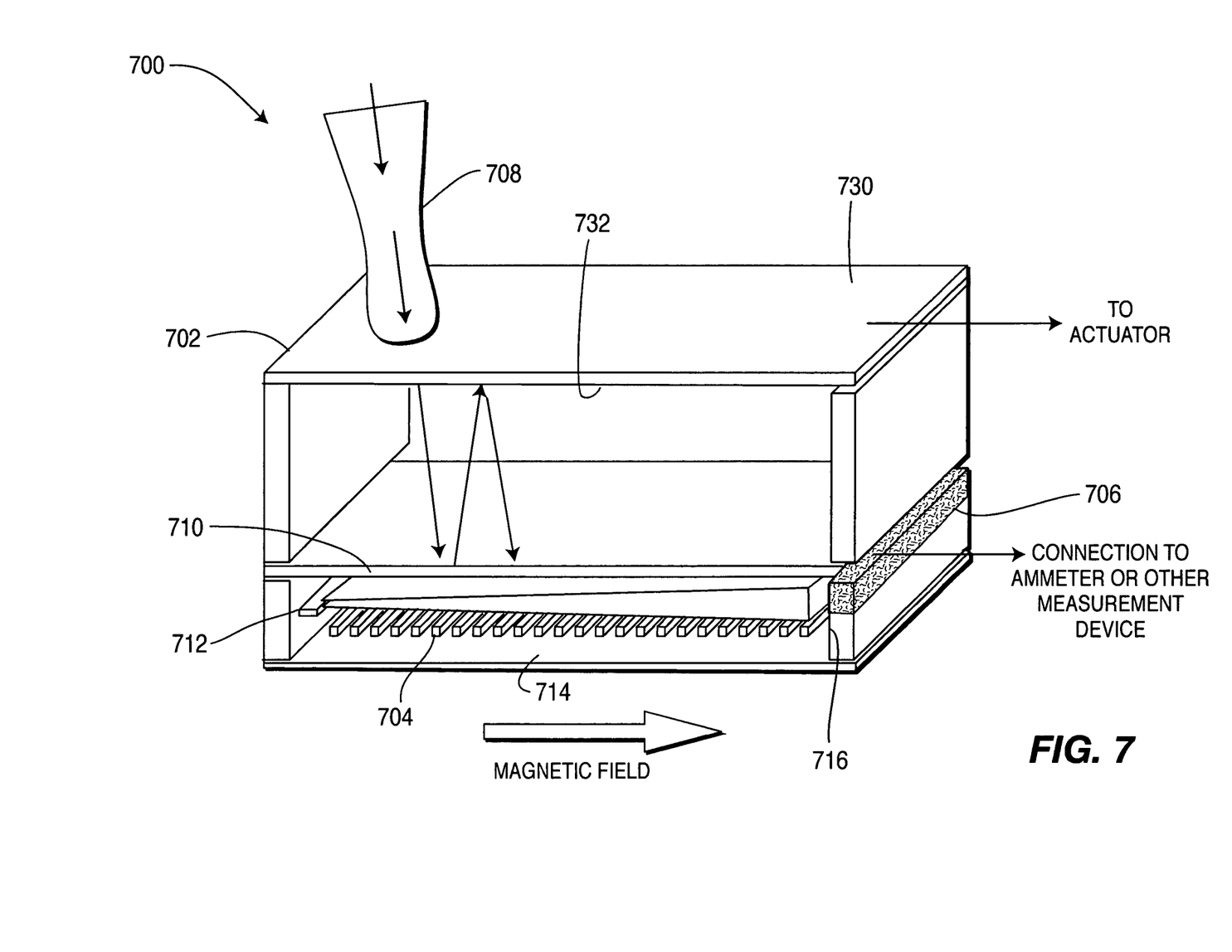
FIG. 7 is a perspective view of an embodiment of a detection system for detecting long wavelength terahertz radiation.

FIG. 7 is a perspective view of an embodiment of a detection system 700 for detecting long wavelength (i.e., low energy) terahertz radiation. The detector 700 is structurally similar to the systems 400 and 500 illustrated in FIGS. 4 and 5 and comprises a microwave cavity 702, a grating 704, a collector 706, an input pipe 708, a terahertz transmissive window 710 and a lid 730. The grating 704 is positioned on a lower surface 714 of the microwave cavity 702, the interior of which is maintained at a vacuum. The collector 706 is positioned at one end 716 of the grating 704, opposite the point of entry 712 for an electron beam. The input pipe 708 is positioned to supply input (e.g., radiation) to the microwave cavity 702 at an angle substantially normal to the grating 704. The lid 730 has a reflective surface 732 that is positioned to face the transmissive window 710.

The detection system 700 works on an "inverse" Smith-Purcell principle. An electron beam is passed closely to the grating 704. The input pipe 708 collects radiation from an environment outside of the microwave cavity 702 and funnels and concentrates the radiation into the microwave cavity 702. Radiation in the terahertz range will pass through the terahertz transmissive layer 710 and hit the grating 704 at an angle substantially normal to the grating 704. If the captured radiation that strikes the grating 704 is of a particular wavelength, the radiation will increase the energy of the electrons in the electron beam. The increase in energy will cause the electrons to change their behavior in a spectrometer. The electron beam is then intercepted by the collector 706, which is connected to a measurement device that observes the increase in energy. In one embodiment, the measurement device is a simple ammeter circuit. The presence of particular wavelengths of radiation in the detector 700 can therefore be detected by observing an increase in the energy of the electron beam, rather than a decrease as is measured by the systems 400 and 500 described above.

In one embodiment, the detection system 700 is used in conjunction with a solid state source of radiation to detect explosives in an outside environment. The detector 700 is tunable to detect a chosen Smith-Purcell absorption band, which is accomplished in one embodiment by varying the period of the grating 704 or the voltage of the electron beam. In another embodiment, the lid 730 is coupled to an actuator so that the position of the reflective surface 732 is variable to control the bands of radiation that are discretized.

Thus the present invention represents a significant advancement in the field of terahertz source technology. A system is provided that enables accurate and efficient detection of chemical and/or biological contaminants. Furthermore, in several embodiments, the invention may be tuned or configured to enhance the accuracy and efficiency of the detection system. The present invention may have further advantages in the fields of imaging, communications and spectroscopy.

While foregoing is directed to the preferred embodiment of the present invention, other and further embodiments of the invention may be devised without departing from the basic scope thereof, and the scope thereof is determined by the claims that follow.

The invention claimed is:

1. A system for detecting contaminants in a sample, comprising:
a concentrator for concentrating molecules of the contaminants in said sample; and
a terahertz radiation detection system coupled to the concentrator for receiving the concentrated molecules for analysis, wherein the concentrator is coupled to the detection system by a sonic orifice.

2. A system for detecting contaminants in a sample, comprising:
a concentrator for concentrating molecules of the contaminants in said sample;
a terahertz radiation detection system coupled to the concentrator for receiving the concentrated molecules for analysis, the detection system comprising
a radiation source for generating frequency modulated far infrared radiation;
a low-pressure cavity coupled to the radiation source for receiving said sample; and
a radiation detector coupled to the low-pressure cavity.

3. The system of claim 2, wherein the low-pressure cavity has one or more far infrared transmissive walls to allow the frequency modulated far infrared radiation to pass therethrough.

4. The system of claim 2, wherein the radiation detector is cryogenically cooled.

5. The system of claim 2, wherein the low-pressure cavity has:
a sample chamber for receiving said sample;
a vacuum chamber,
a terahertz transmissive window positioned between the sample chamber and the vacuum chamber; and
a conductive grating disposed within the vacuum chamber.

6. The system of claim 5, wherein the low-pressure cavity further comprises:
a lid having a reflective surface positioned opposite to the terahertz transmissive window.

7. The system of claim 6, wherein the lid is coupled to an actuator for controlling the position of the lid.

8. The system of claim 5, wherein the low-pressure cavity further comprises:
a collector positioned proximate to an end of the conductive grating for intercepting an electron beam passed over the conductive grating.

9. The system of claim 8, wherein the collector is coupled to a measurement device for measuring the energy of the electron beam.

10. The system of claim 9, wherein the measurement device is an ammeter circuit.

11. The system of claim 5, wherein the sample chamber further comprises:
a sample tube for containing a liquid in which said sample is suspended.

12. The system of claim 5, wherein the low-pressure cavity further comprises:
an input pipe coupled to for sample chamber for collecting radiation from
an environment outside of the low-pressure cavity and funneling said radiation into the sample chamber.

13. The detector of claim 5, wherein the sample chamber further comprises:

a sample tube for containing a liquid in which said sample is suspended.

14. The system of claim 2, wherein the radiation source is an IMPATT multiplier.

15. A detector for detecting contaminants in a sample comprising:
a radiation source for generating frequency modulated terahertz radiation;
a low-pressure cavity coupled to the radiation source for containing said sample; and
a radiation detector coupled to the low-pressure cavity for measuring absorption of radiation by said sample for determining whether said contaminant is in said sample.

16. The detector of claim 15, wherein the low-pressure cavity has one or more far infrared transmissive walls to allow the frequency modulated far infrared radiation to pass therethrough.

17. The detector of claim 15, wherein the radiation detector is cryogenically cooled.

18. The detector of claim 15, wherein the low-pressure cavity comprises: a sample chamber for receiving said sample;
a vacuum chamber,
a terahertz transmissive window positioned between the sample chamber and the vacuum chamber; and
a conductive grating disposed within the vacuum chamber.

19. The detector of claim 18, wherein the sample chamber has:
a lid having a reflective surface positioned opposite to the terahertz transmissive window.

20. The detector of claim 19, wherein the lid is coupled to an actuator for controlling the position of the lid.

21. The detector of claim 18, wherein the low-pressure cavity further comprises; a collector positioned proximate to an end of the conductive grating for intercepting an electron beam passed over the conductive grating.

22. The detector of claim 21, wherein the collector is coupled to a measurement device for measuring the energy of the electron beam.

23. The detector of claim 22, wherein the measurement device is an ammeter circuit.

24. The detector of claim 18, wherein the low-pressure cavity further comprises:
an input pipe coupled to the sample chamber for collecting radiation from an environment outside of the low-pressure cavity and funneling said radiation into the sample chamber.

25. The detector of claim 15, wherein the radiation source is an IMPATT multiplier.

26. A method for detecting contaminant molecules in a sample, comprising:
introducing the sample into a first portion of a low-pressure cavity;
applying terahertz radiation to the sample; and
observing the interaction of the terahertz radiation with the sample, for detecting the presence of the contaminant molecules.

27. The method of claim 26, further comprising:
concentrating the sample to enhance contaminant molecule density prior to introducing the sample into the low-pressure cavity.

28. The method of claim 26, wherein the sample is introduced into the first portion of the low-pressure cavity in a gaseous state.

29. The method of claim 28, wherein the step of observing the interaction of the terahertz radiation with molecules in the sample comprises:
providing a conductive grating disposed in a second portion of the low-pressure cavity, wherein the second portion of the low-pressure cavity is physically isolated from the first portion by a terahertz transmissive window; and
passing an electron beam over the conductive grating, in close proximity to the conductive grating; and
determining the amount of energy lost by the electron beam.

30. The method of claim 28, wherein the step of observing the interaction of the terahertz radiation with molecules in the sample:
providing a conductive grating disposed in a portion of the low-pressure cavity;
passing an electron beam over the conductive grating, in close proximity to the conductive grating;
funneling radiation from an environment outside of the low-pressure cavity into the low-pressure cavity; and
determining the amount of energy gained by the electron beam.

31. The method of claim 26, wherein the sample is introduced into the low-pressure cavity in a liquid state.

32. The method of claim 31, wherein the step of observing the interaction of the terahertz radiation with molecules in the sample comprises:
introducing a portion of the sample into a first liquid to form a first liquid solution;
inserting the first liquid solution into a container disposed within the first portion of the low-pressure cavity;
observing the rotational spectrum of the molecules in the first liquid solution;
introducing a portion of the sample into a second liquid to form a second liquid solution, wherein the second liquid contains at least one binding agent for binding to the molecules in the sample;
inserting the second liquid solution into the container disposed within the first portion of the low-pressure cavity; and
observing the rotational spectrum of the molecules in the second liquid solution; and
comparing the rotational spectra of the first and second liquid solutions.

33. The method of claim 32, wherein the step of observing the rotational spectra of the first and second liquid solutions comprises:
providing a conductive grating disposed in a second portion of the low-pressure cavity, wherein the second portion of the low-pressure cavity is physically isolated from the first portion by a terahertz transmissive window;
passing an electron beam over the conductive grating, in close proximity to the conductive grating; and
determining the amount of energy lost by the electron beam.

34. The method of claim 26, wherein the step of applying terahertz radiation to the sample comprises modulating the frequency of the terahertz radiation.

* * * * *